United States Patent
Fairhurst et al.

(10) Patent No.: US 6,844,338 B2
(45) Date of Patent: Jan. 18, 2005

(54) PIPERIDYINDOLES AS SEROTONIN RECEPTOR LIGANDS

(75) Inventors: John Fairhurst, Hampshire (GB); Peter Gallagher, Hampshire (GB)

(73) Assignee: Eli Lilly and Company, Indianapolis, IN (US)

( * ) Notice: Subject to any disclaimer, the term of this patent is extended or adjusted under 35 U.S.C. 154(b) by 57 days.

(21) Appl. No.: 10/258,356

(22) PCT Filed: May 4, 2001

(86) PCT No.: PCT/US01/11744
§ 371 (c)(1), (2), (4) Date: Oct. 21, 2002

(87) PCT Pub. No.: WO01/87881
PCT Pub. Date: Nov. 22, 2001

(65) Prior Publication Data
US 2003/0225068 A1 Dec. 4, 2003

(30) Foreign Application Priority Data
May 18, 2000 (GB) .............................. 0012082

(51) Int. Cl.[7] .................... C07D 401/14; C07D 417/14; A61K 31/5415; A61K 31/517; A61P 25/24
(52) U.S. Cl. ................. 514/222.8; 514/226.5; 514/266.22; 514/312; 514/322; 514/323; 544/11; 544/49; 544/284; 546/158; 546/198; 546/199; 546/201
(58) Field of Search .................. 544/11, 49, 284; 546/158, 198, 199, 201; 514/222.8, 226.5, 266.22, 312, 318, 322, 323

(56) References Cited

U.S. PATENT DOCUMENTS

5,670,511 A 9/1997 Marz et al. ................ 514/290

FOREIGN PATENT DOCUMENTS

| | | |
|---|---|---|
| DE | 195 00 689 | 7/1996 |
| EP | 0 013 612 | 7/1980 |
| EP | 0 350 403 | 1/1990 |
| EP | 0 536 419 | 10/1992 |
| EP | 0 897 921 | 2/1999 |
| EP | 1 106 605 | 6/2001 |
| FR | 2 621 588 | 4/1989 |
| FR | 2 675 801 | 10/1992 |
| WO | WO 99/58525 | 11/1999 |
| WO | WO 00/31074 | 6/2000 |
| WO | WO 00/49017 | 8/2000 |
| WO | WO 00/78716 | 12/2000 |

OTHER PUBLICATIONS

Thomas A. Godwin (Gastrointestinal Diseases, <http://edcenter.med.cornell.edu/CUMC_PathNotes/Gastrointestinal/Gastrointestinal.html>, 51 pages) downloaded on Jun. 4, 2004.*

* cited by examiner

Primary Examiner—Mukund J. Shah
Assistant Examiner—Kahsay Habte
(74) Attorney, Agent, or Firm—Manisha A. Desai

(57) ABSTRACT

A pharmaceutical compound of the formula (I) in which $R^1$ and $R^2$ are each hydrogen or $C_{1-6}$ alkyl, $R^3$ is —$SR^{10}$, —$SOR^{10}$, —$SO_2R^{10}$, —$COR^{10}$, —$CH_2OH$ or —$CONHR^{11}$, where $R^{10}$ is $C_{1-6}$ alkyl and $R^{11}$ is hydrogen or $C_{1-6}$ alkyl, $R^4$, $R^5$, $R^6$ and $R^7$ are each hydrogen or $C_{1-6}$alkyl, provided that at least one of $R^4$, $R^5$, $R^6$ and $R^7$ is $C_{1-6}$alkyl, $R^8$ and $R^9$ are each hydrogen, halo, $C_{1-6}$ alkyl or cyano, n is 0 or 1 and m is 2 or 3, x is a (a) or (b), and y is (c) or (d), wherein $R^{12}$ and $R^{13}$ are each hydrogen, $C_{1-}$ alkyl, cyclopropyl or cyclopropyl-$C_{1-6}$ alkyl; and salts thereof.

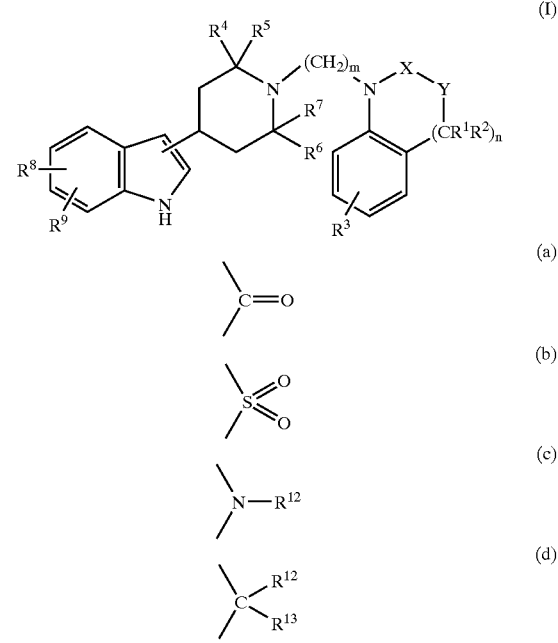

8 Claims, No Drawings

PIPERIDYINDOLES AS SEROTONIN RECEPTOR LIGANDS

This invention relates to pharmaceutical compounds and their use in the treatment of disorders of the central nervous system.

It is well known that compounds active at serotonin receptors have potential in the treatment of disorders of the central nervous system and, for example, certain halo-substituted indole compounds having serotonin antagonist properties are disclosed in WO 98/31686.

The compounds of the invention have the following formula:

(I)

in which $R^1$ and $R^2$ are each hydrogen or $C_{1-6}$ alkyl,
$R^3$ is $—SR^{10}$, $—SOR^{10}$, $—SO_2R^{10}$, $—COR^{10}$, $—CH_2OH$ or $—CONHR^{11}$, where $R^{10}$ is $C_{1-6}$ alkyl and $R^{11}$ is hydrogen or $C_{1-6}$ alkyl,
$R^4$, $R^5$, $R^6$ and $R^7$ are each hydrogen or $C_{1-6}$ alkyl, provided that at least one of $R^4$, $R^5$, $R^6$ and $R^7$ is $C_{1-6}$ alkyl,
$R^8$ and $R^9$ are each hydrogen, halo, $C_{1-6}$ alkyl or cyano,
n is 0 or 1 and m is 2 or 3,
X is $$\diagup_{\diagdown} C=O \quad \text{or} \quad \diagup_{\diagdown} S\diagup_{\diagdown}^{O}_{O},$$

and
Y is $$\diagup_{\diagdown} N—R^{12} \quad \text{or} \quad \diagup_{\diagdown} C\diagdown^{R^{12}}_{R^{13}}$$

wherein $R^{12}$ and $R^{13}$ are each hydrogen, $C_{1-6}$ alkyl, cyclopropyl or cyclopropyl-$C_{1-6}$ alkyl;
and salts thereof.

The compounds of the invention and their pharmaceutically acceptable salts are indicated for use in the treatment of disorders of the central nervous system.

Accordingly, the present invention also provides the ue of a compound of the present invention in the preparation of a medicament for the treatment of a disorder of the central nervous system.

In the above formula (I), a halo atom is preferably chloro, bromo or fluoro, and is especially fluoro. A $C_{1-6}$ alkyl group can be methyl, ethyl, propyl, butyl or pentyl or hexyl, and can be branched or unbranched including isopropyl and tert. butyl.

Preferred compounds are those which have one or more of the following features:
(i) $R^8$ and $R^9$ are each hydrogen or halo;
(ii) $R^8$ and $R^9$ are each hydrogen or fluoro;
(iii) $R^8$ is fluoro and $R^9$ is hydrogen;
(iv) $R^8$ is fluoro in the 6-position, and $R^9$ is hydrogen;
(v) X is $$\diagup_{\diagdown} S\diagup_{\diagdown}^{O}_{O};$$

(vi) Y is $$\diagup_{\diagdown} C\diagdown^{R^{12}}_{R^{13}}$$

wherein $R^{12}$ and $R^{13}$ are both $C_{1-6}$ alkyl;

(vii) Y is $$\diagup_{\diagdown} N—R^{12}$$

where $R^{12}$ is $C_{1-6}$ alkyl, especially isopropyl;

(viii) n is 1 and $R^1$ and $R^2$ are both hydrogen;
(ix) $R^3$ is at the 6-position or the 7-position, preferably at the 6-position;
(x) $R^3$ is $—SOR^{10}$, $—SO_2R^{10}$ or $—COR^{10}$;
(xi) $R^{10}$ is methyl or ethyl, and especially methyl;
(xii) $R^3$ is $—SOCH_3$ or $—SO_2CH_3$, at the 6-position or the 7-position, preferably at the 6-position;
(xiii) the point of attachment of the piperidine group is at the 3-position on the indole moiety;
(xiv) $R^4$ is $C_{1-6}$ alkyl.

A preferred group of compounds is of the following formula:

in which $R^8$ and $R^9$ are each hydrogen or halo, preferably fluoro,
$R^3$ is at the 6- or 7- position and is $—SOR^{10}$, $—SO_2R^{10}$ or $—COR^{10}$, where $R^{10}$ is $C_{1-6}$ alkyl,
$R^4$ is $C_{1-6}$ alkyl, and
$R^{12}$ is $C_{1-6}$ alkyl; and salts thereof.

A further preferred group of compounds is of the following formula

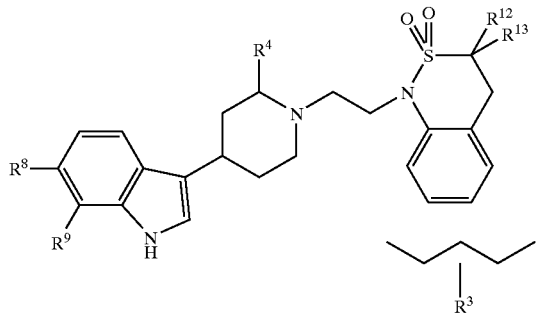

in which
R$^8$ and R$^9$ are each hydrogen or halo, preferably fluoro,
R$^3$ is in the 6- or 7-position and is —SOR$^{10}$, —SO$_2$R$^{10}$ or —COR$^{10}$, where R$^{10}$ is C$_{1-6}$ alkyl,
R$^4$ is C$_{1-6}$ alkyl, and
R$^{12}$ and R$^{13}$ are each hydrogen or C$_{1-6}$ alkyl; and salts thereof.

A further preferred group of compounds is of the following formula:

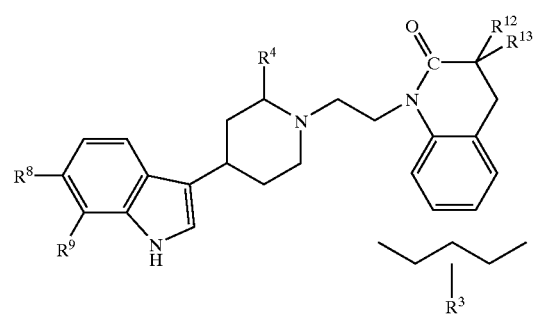

in which
R$^8$ and R$^9$ are each hydrogen or halo, preferably fluoro,
R$^3$ is in the 6- or 7-position and is —SOR$^{10}$, —SO$_2$R$^{10}$ or —COR$^{10}$, where R$^{10}$ is C$_{1-6}$ alkyl,
R$^4$ is C$_{1-6}$ alkyl, and
R$^{12}$ and R$^{13}$ are each hydrogen or C$_{1-6}$ alkyl; and salts thereof.

A further preferred group of compounds is of the following formula:

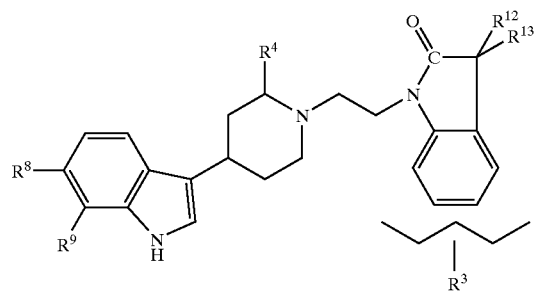

in which
R$^8$ and R$^9$ are each hydrogen or halo, preferably fluoro,
R$^3$ is in the 6- or 7-position and is —SOR$^{10}$, —SO$_2$R$^{10}$ or —COR$^{10}$, where R$^{10}$ is C$_{1-6}$ alkyl,
R$^4$ is C$_{1-6}$ alkyl, and
R$^{12}$ and R$^{13}$ are each hydrogen or C$_{1-6}$ alkyl; and salts thereof.

As indicated above, it is, of course, possible to prepare salts of the compound of the invention and such salts are included in the invention. Acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, pyruvic, lactobionic, glycollic, maleic, hydroxymaleic, fumaric, malic, tartaric, citric, salicyclic, o-acetoxybenzoic, or organic sulphonic, 2-hydroxyethane sulphonic, toluene-p-sulphonic, naphthalene-2-sulphonic, bisethanesulphonic acid or methanesulphonic acid. A preferred salt is the tartrate.

In addition to the pharmaceutically acceptable salts, other salts are included in the invention. They may serve as intermediates in the purification of compounds or in the preparation of other, for example pharmaceutically acceptable, acid addition salts, or are useful for identification, characterisation or purification.

Some of the compounds of the invention contain one or more asymmetric carbon atoms which gives rise to isomers. Moreover, compounds which are substituted by a sulphinyl group (R$^3$ is —SOR$^{10}$) also exist in isomeric forms. These compounds are normally prepared as racemic mixtures and can conveniently be used as such, but individual isomers can be isolated by conventional techniques, if so desired. Such racemic mixtures and individual optical isomers form part of the present invention. It is preferred to use an enantiomerically pure form.

The invention also includes a process for producing a compound of formula (I) above, which comprises reacting a compound of the formula:

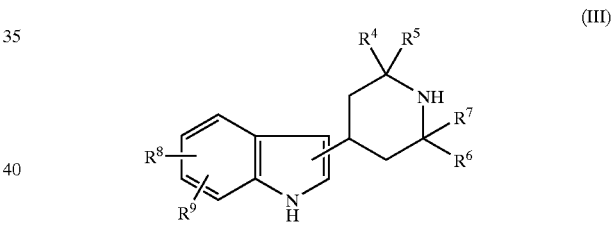

with a compound of the formula

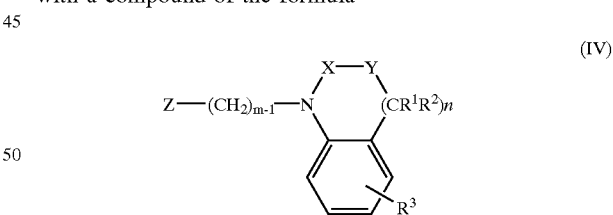

where n and m, and the substituents, have the values given above, and (i) Z is —CH$_2$W, where W is a leaving group such as, for example, a halo atom or a mesylate or tosylate, or (ii) Z is —CHO.

The reaction is preferably carried out in a polar solvent such as, for example, acetonitrile or water, at a temperature of from 50° C. to 150° C., and in the presence of sodium iodide and a base such as, for example, sodium carbonate. When an aldehyde intermediate is employed, the reaction is one of reductive amination using, for example, sodium cyanoborohydride, borane in pyridine or triacetoxy borohydride in the presence of the compound of formula (III).

The intermediate compounds of formula (III) can be made by reacting an indole with the appropriate piperidinone.

Compounds of formula (VI) can be prepared by reacting an ethane derivative of the formula V—(CH$_2$)$_m$—W (V), where V is halo, preferably bromo, with a compound of formula:

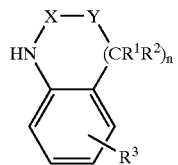

(VI)

Preferred ethane derivatives of formula (V) are dihaloethanes, for instance bromo chloroethane, and the reaction is preferably carried out in an organic solvent such as, for example, dimethyl formamide, with a strong base such as sodium hydride, at a temperature of from 0° C. to 100° C., for instance room temperature.

Aldehyde intermediates of formula (IV) can be prepared from the appropriate alkene by oxidation employing, for example, ozone or osmium tetroxide.

Alternatively, compounds of formula (VI) can be prepared by a synthetic route, such as the following:

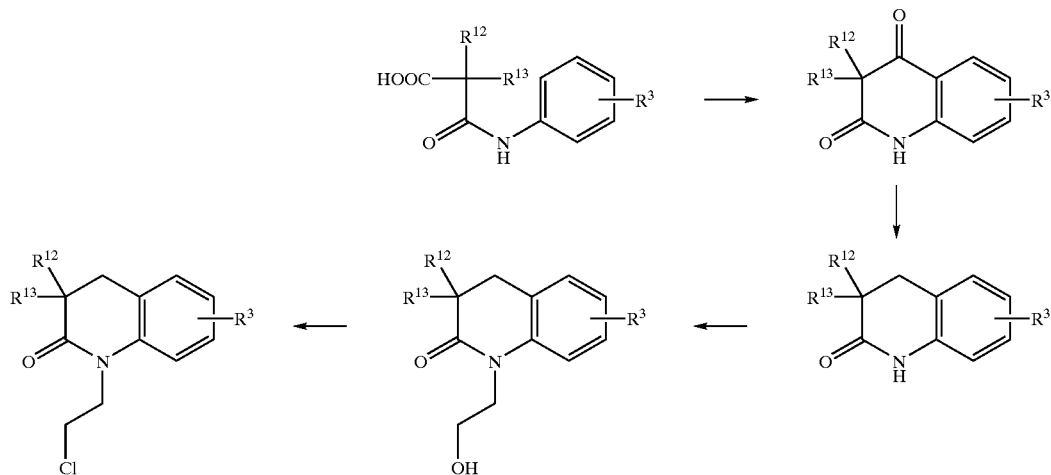

or by the following route:

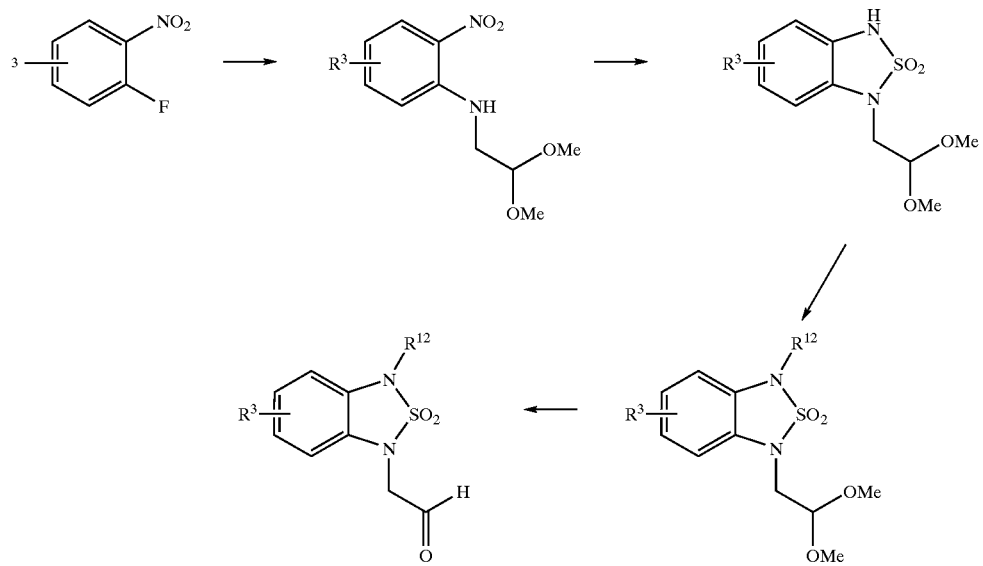

The intermediate compounds of formula (VI) are known in the literature, and they can readily be prepared by a variety of routes as, for example, in the case of compounds of formula (VI) having the following structure:

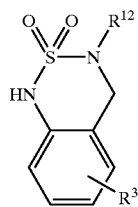
(VIII)

the principal route of synthesis is by means of a reaction between the appropriate sulfamoyl compound prepared from an aniline and sulfamoyl chloride and trioxan, in the presence of an acid, for example, an alkyl sulfonic acid:

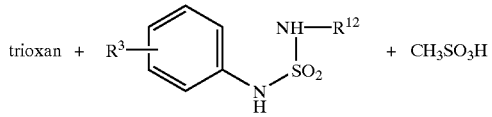

Alternatively, compounds of formula (VII) can be synthesised by reaction of sulfamide with an amino benzylamine in pyridine or diglyme. The amino benzylamine can be prepared in three steps from the appropriate nitrobenzoic acid via amide formation and a two step reduction as, for example:

A further alternative route to compounds of formula (VII) involves the use of an appropriate N-sulfamoyloxazolidinone of formula:

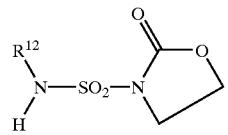

which can be readily prepared by reacting chlorosulfonyl-isocyanate and amine with chloro- or bromo-ethanol. The N-sulfamoyloxazolidinone is then reacted with an aniline of formula

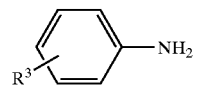

and the resulting sulfonyl urea reacted with trioxan, as described above, to give the compound of formula (VII).

An alternative route to the compounds of the invention in which in formula (I) X is:

consists of an analogous, reverse, condensation of the two principal components of the molecule as, for example, by reacting a compound of the formula:

(VIII)

with a compound of formula (VII) above, employing the Mitsunobu reaction. The reaction is carried out in an organic solvent such as tetrahydrofuran or dimethyl formamide, at a temperature of, for example, 0 C. to 5 C. employing a dialkylazodicarboxylate and triphenylphosphine or tributylphosphine. Intermediate compounds of formula (VIII) are novel and are included as part of the present invention.

It will be appreciated that in preparing compounds of formula (I) in which $R^3$ is —$SOR^{10}$ or —$SO_2R^{10}$, the appropriate intermediates as, for example, those of formula (VII), can be prepared by oxidation of the —$SR^{10}$ substituted compound, by the use of metachloro perbenzoic acid or Oxone® or sodium perborate or osmium tetroxide/sodium periodate.

As mentioned above, the compounds of the invention and their pharmaceutically acceptable salts have useful central nervous system activity. They have been shown to increase release of tritiated-5HT from guinea pig cortical slices in a test with the following procedure.

Cortical slices from the brains of male guinea pigs were incubated with 50 nM [$^3$H]-5-HT for 30 minutes at 37° C. The slices were washed in basal buffer containing 1 μm paroxetine and then transferred to baskets. The baskets were used to transfer the tissue between the washing and release buffers, all of which contained 1 μM paroxetine.

In order to obtain a stable baseline release, the slices were incubated for 11 minutes in buffer and then transferred for 4 minutes to a second tube containing buffer. Following incubation they were again transferred, for a further 4 minutes, to a buffer in which NaCl had been substituted, on an equimolar basis, to give a KCl concentration of 30 mM (release sample). The tritium in the tissue samples and in the buffers from the three incubation periods was estimated by liquid scintillation spectroscopy. Test compound was present throughout the three incubation periods. The compounds of the invention enhanced release of 5-HT.

Compounds of the invention have been demonstrated to be active at the serotonin 1B and 1D receptors. Their activity may be demonstrated in tests as described in Pullar, I. A. et al, European Journal of Pharmacology, 407, 39–46.

Compounds of the invention have also been demonstrated to be active at the serotonin, $5-HT_{2A}$, receptor. Their binding activity has been demonstrated in a test described by Nelson, D. L. et al, J. Pharmacol. Exp. Ther., 265, 1272–1279, in which the affinity of the compound for the human 2A receptor is measured by its ability to displace the ligand [$^3$H]-ketanserin.

Compounds of the invention are also active serotonin reuptake inhibitors as measured by their displacement of [$^3$H]-paroxetine at the reuptake site, Neuropharmacology Vol. 32 No. 8, 1993, pages 737–743.

Because of their ability to enhance 5-HT release as well as selective affinity for 5-HT receptors, the compounds of the present invention are indicated for use in treating a variety of conditions such as depression, obesity, bulimia, alcoholism, pain, hypertension, ageing, memory loss, sexual dysfunction, anxiety, schizophrenia, gastrointestinal disorders, headache, cardiovascular disorders, smoking cessation, drug addiction, emesis, epilepsy, Alzheimer's and sleep disorders. Compounds of the present invention may be particularly useful in the treatment of depression. Compounds of the invention may also be useful for the treatment of obsessive compulsive disorder.

The present invention also provides a method of treating a warm blooded mammal including a human suffering from or susceptible to a disorder of the central nervous system, which comprises administering to said human an effective amount of a compound of the present invention, or a pharmaceutically acceptable salt thereof.

The present invention further provides a method of inhibiting the 5-HT2A receptor which comprises administering to a warm blooded mammal including a human in need of such treatment a therapeutically effective amount of a 5-HT2A antagonist of formula I.

The present invention also provides a method of inhibiting the reuptake of serotonin, which comprises administering to a warm blooded mammal including a human in need of such treatment a therapeutically effective amount of a serotonin reuptake inhibitor of formula I.

The compounds of the invention are effective over a wide dosage range, the actual dose administered being dependent on such factors as the particular compound being used, the condition being treated and the type and size of mammal being treated. However, the dosage required will normally fall within the range of 0.01 to 20 mg/kg per day, for example in the treatment of adult humans, dosages of from 0.1 to 100 mg per day may be used, preferably from 2 to 20 mg per day as, for example, for the preferred compounds of formula (II) and (III).

The compounds of the invention will normally be administered orally or by injection and, for this purpose, the compounds will usually be utilised in the form of a pharmaceutical composition. Such compositions are prepared in a manner well known in the pharmaceutical art and comprise at least one active compound.

Accordingly the invention includes a pharmaceutical composition comprising as active ingredient a compound of formula (I) or a pharmaceutically acceptable salt or ester thereof, associated with a pharmaceutically acceptable excipient. In making the compositions of the invention, the active ingredient will usually be mixed with a carrier, or diluted by a carrier, or enclosed within a carrier which may be in the form of a capsule, sachet, paper or other container. The excipient may be a solid, semi-solid or liquid material which acts as a vehicle, excipient or medium for the active ingredient. Some examples of suitable excipients are lactose, dextrose, sucrose, sorbitol, mannitol, starches, gum acacia, calcium phosphate, alginates, tragacanth, gelatin syrup, methyl cellulose, methyl- and propyl-hydroxybenzoate, talc, magnesium stearate or oil. The compositions of the invention may, if desired, be formulated so as to provide quick, sustained or delayed release of the active ingredient after administration to the patient.

Depending on the route of administration, the foregoing compositions may be formulated as tablets, capsules or suspensions for oral use and injection solutions or suspensions for parenteral use or as suppositories. Preferably the compositions are formulated in a dosage unit form, each dosage containing from 0.1 to 100 mg, more usually 2 to 20 mg, of the active ingredient.

The following Preparations and Examples illustrate routes to the synthesis of the compounds of the invention.

EXAMPLES

1-Dimethylamino-2-(4-fluoro-2-nitro)phenylethene

A mixture of 4-fluoro-2-nitrotoluene (50 g, 0.32 mol), dimethylformamide dimethylacetal (76.77 g) and dimethylformamide (910 ml) were heated under reflux under nitrogen with stirring for 7 hr, cooled, allowed to stand for 16 hr, poured into ice-water (2 l), stirred for 15 mins and the resultant precipitate isolated by filtration, washed with water (500 ml), dried to give a red solid. (Org. Synth. (1985), 63, 214–25)

6-Fluoro-1H-indole

A 40 liter Cook hydrogenator was charged under a nitrogen atmosphere with 10% palladium on charcoal (9 g) suspended in toluene (400 ml). To this suspension was added 1-dimethylamino-2-(4-fluoro-2-nitro) phenylethene (137.2 g, 0.653 mol) in toluene (1.4 l) and the mixture hydrogenated at 80 psi for 3.5 hr. The suspension was then filtered through a celite pad, which was washed through with toluene (2×200 ml) and the filtrate and washings evaporated under reduced pressure to give a brown oil which crystallised on standing to a yellow brown solid 93.65 g. This solid was dissolved in ethyl acetate-hexane (7:3) and filtered through a pad of flash silica. The required fractions were collected and evaporated under reduced pressure to give a pale brown solid. (Org. Synth. (1985), 63, 214–25)

Similarly prepared were:

6,7-Difluoro-1H-indole

δ ($^1$H NMR, CDCl$_3$, ppm): 6.50 (1H, m), 6.90 (1H, m), 7.30 (2H, m), 8.4 (1H, br).

6-Fluoro-7-methyl-1H-indole (J. Med. Chem., 1976 19(3) 391–5)

δ ($^1$H NMR, CDCl$_3$, ppm): 2.4 (3H, s), 6.50 (1H,), 6.90 (1H, t), 7.20 (1H, m), 7.4 (1H, m), 0.0 (1H, s).

6-Fluoro-3-(6-methyl-1,2,3,6-tetrahydro-4-pyridinyl)-1H-indole and 6-fluoro-3-(2-methyl-1,2,3,6-tetrahydro-4-pyridinyl)-1H-indole Powdered potassium hydroxide (4.01 g, 71.5 mmol) is dissolved in a mixture of methanol (70 ml) and water (1 ml), and stirred until no solid remains. 6-Fluoro indole (1.10 g, 8.73 mmol) and 2-methylpiperidone trifluoroacetic acid salt (4.18 g, 18.4 mol) [2-methyl 4-piperidones can be synthesised by known methods in the literature for example Mistryukov, E. A.; Aronova, N. I. Izv. Akad. Nauk SSSR, Ser. Khim. (1966), (12), 2171–6.] are added as single portions, and the mixture is heated to reflux under a nitrogen atmosphere for four hours, before being allowed to cool to 50° C. Water (70 ml) is then added in a dropwise manner over 20 mins, and. the mixture is then stirred for a further 1 hour, during which time the temperature falls to r.t. The yellow precipitate that forms is collected by vacuum filtration, rinsed with a small amount of cold water, then dried in vacuo at 60° C. for 16 hours. This affords 1.60 g, (79.7%) of the title compound in a ratio of 2:1 for the regioisomers.

$^1$H NMR (CDCl$_3$), δ (ppm); 1.22–1.34 (2×d, 3H) 2.12–2.60 (m, 2.5 H), 2.92–3.8 (m, 2.5H), 3.68 (br.s 1H), 6.10 (s, 0.33H), 6.22 (s, 0.67H), 6.82–6.98 (t, 1H), 7.00–7.10 (d, 1H), 7.14 (s, 1H), 7.74 (m, 1H), 8.34 (br.s, 1H); MS, reqd. 230.1; obs. 231.1 (M+1; FIAPOS); 229.1 (M−1; FIANEG)

Similarly prepared were 6,7-Difluoro-3-(6-methyl-1,2,3,6-tetrahydro-4-pyridinyl)-1H-indole) and 6,7-difluoro-3-(2-methyl-1,2,3,6-tetrahydro-4-pyridinyl)-1H-indole $^1$H NMR (CD$_3$OD), (ppm); 1.40 (m, 3H), 2.32–2.84 (m, 2H), 3.06–3.32 (m, 1H), 3.34–3.58 (m, 1H), 3.64–3.88 (m, 1H), 6.22 (s, 0.28H), 6.40 (s,.0.72H), 7.04–7.20 (m, 1H), 7.50 (s, 1H), 7.70–7.78 (s, 1H); MS, reqd. 248.1; obs. 249.1 (M+1; FIAPOS); 247.1 (M−1; FIANEG).

6-Fluoro-7-methyl-3-(6-methyl-1,2,3,6-tetrahydro-4-pyridinyl)-1H-indole) and 6,7-difluoro-3-(2-methyl-1,2,3,6-tetrahydro-4-pyridinyl)-1H-indole $^1$H NMR ((CD$_3$)$_2$SO), δ (ppm); 1.30–1.44 (m, 3H), 2.20–2.40 (m, 1H), 2.54 (s, 3H), 3.04–3.86 (m, 4H), 6.14–6.24 (m, 1H), 6.98–7.10 (m, 1H), 7.52–7.72 (s, 1H), 7.72–7.82 (m, 1H).

tert-Butyl 4-(6-fluoro-1H-indol-3-yl)-6-methyl-3,6-dihydro-1(2H)-pyridinecarboxylate and tert-butyl 4-(6-fluoro-1H-indol-3-yl)-2-methyl-3,6-dihydro-1(2H)-pyridinecarboxylate Di-tert butyl dicarbonate (5.90 g, 0.027 mol) is dissolved in THF at 0° C., and a mixture 6-fluoro-3-(6-methyl-1,2,3,6-tetrahydro-4-pyridinyl)-1H-indole and 6-fluoro-3-(2-methyl-1,2,3,6-tetrahydro-4-pyridinyl)-1H-indole (5.17 g, 0.022 mol) is added portionwise over 5 minutes. The mixture is stirred at this temperature for 1 hour, then for 3 hours at room temperature, before 100 ml aqueous sodium bicarbonate (sat. solution) is added. This mixture is extracted with ethyl acetate (3×100 ml), then the combined organic layers are dried over MgSO$_4$, before the solvent is removed in vacuo. The residual pale yellow oil is passed through a silica pad, eluted with dichloromethane, then 10% methanol, 90% dichloromethane, to give 7.36 g, 100% of the desired product after removal of the solvent. The ratio of regioisomers is 2:1.

$^1$H NMR (CDCl$_3$), δ (ppm); 1.18 (d, 3H), 1.50 (s, 9H), 2.20–2.30 (br. d, 1H), 2.76–2.90 (br. d, 1H), 3.72–3.82 (br. d, 1H), 4.30–4.54 (br d, 1H), 4.64 (m, 1H), 6.10 (br. s, 1H), 6.90 (t, 1H), 7.06 (d, 1H), 7.12 (s, 1H), 7.74 (m, 1H), 8.54 (m, 1H); MS, reqd. 330.1; obs. 331.1 (M+1; FIAPOS); 329.1 (M−1; FIANEG)

Similarly prepared were tert-Butyl 4-(6,7-difluoro-1H-indol-3-yl)-6-methyl-3,6-dihydro-1(2H)-pyridinecarboxylate and tert-butyl 4-(6,7-difluoro-1H-indol-3-yl)-2-methyl-3,6-dihydro-1(2H)-pyridinecarboxylate $^1$H NMR (CDCl$_3$), (ppm); 1.20–1.28 (m, 3H), 1.44 (s, 9H), 1.84–2.10 (m, 1H), 2.12–2.58 (m, 1H), 2.60–3.16 (m, 1H), 3.62–3.84 (m, 1H), 4.22–4.82 (m, 1H), 6.08 (br. s, 1H), 6.88–7.00 (m, 1H), 7.00–7.12 (m, 1H), 7.38–7.60 (m, 1H); MS, reqd. 348.1; obs. 347.1 (M−1; FIANEG).

tert-Butyl 4-(6-fluoro-7-methyl-1H-indol-3-yl)-6-methyl-3,6-dihydro-1(2H)-pyridinecarboxylate and tert-butyl 4-(6-fluoro-7-methyl-1H-indol-3-yl)-2-methyl-3,6-dihydro-1(2H)-pyridinecarboxylate $^1$H NMR (CDCl$_3$), δ (ppm); 1.18–1.32 (m, 3H), 1.50 (s, 9H), 2.20–2.70 (m, 4H), 2.78–3.14 (m, 1H), 3.60–3.86 (m, 1H), 4.04–4.72 (m, 2H), 6.02–6.12 (m, 1H), 6.82–6.94 (m, 1H), 7.10–7.12 (m, 1H), 7.54–7.62 (m, 1H), 7.96 (br. s, 1H).

tert-Butyl 4-(6-fluoro-1H-indol-3-yl)-(2S,4R)-2-methyl-1-piperidinecarboxylate and tert-butyl 4-(6-fluoro-1H-indol-3-yl)-(2R, 4S)-2-methyl-1-piperidinecarboxylate A mixture of of tert-butyl 4-(6-fluoro-1H-indol-3-yl)-6-methyl-3,6-dihydro-1(2H)-pyridine carboxylate and tert-butyl 4-(6-fluoro-1H-indol-3-yl)-2-methyl-3,6-dihydro-1 (2H)-pyridine carboxylate (2.06 g, 6.24 mmol) is dissolved in dry ethanol (40 ml), along with a suspension of 10% palladium on carbon (0.50 g). This mixture is agitated under 70 psi pressure of hydrogen gas for 16 hours, before the catalyst is removed by filtration through a celite plug. The solvent is removed in vacuo, and the residue purified by column chromatography, using 25% ethyl acetate, 75% hexane as the eluent. After removal of the solvent, this affords 1.21 g, 58% yield of tert-butyl 4-(6-fluoro-1H-indol-3-yl)-2-methyl-1-piperidinecarboxylate as a mixture of cis and trans products. This mixture is subjected to preparative HPLC, firstly using an achiral column (Kromasil KR60-5SIL column, eluted with 89% hexane, 9% dichloromethane, 2% ethanol and 0.1% dimethylamine) to separate the trans and cis isomers (retention times=11.6 and 12.2 min), then using a chiral stationary phase column (Chiralcel-OJ column, eluted with 60% hexane, 40% ethanol and 0.2% dmea) to resolve the two trans enantiomers (retention times=9.1 and 10.5 min). $^1$H NMR (CDCl$_3$), δ (ppm); 1.28 (d, 3H), 1.50 (s, 9H), 1.82–2.06 (m, 3H), 2.88–3.22 (m, 3H), 4.00–4.20 (br. m, 1H), 4.50–4.66 (br. m, 1H), 6.88 (t, 1H), 6.92 (s, 1H), 7.04 (d, 1H), 7.52 (m, 1H), 8.20 (br. s, 1H); MS, reqd. 332; obs. 331.1 (M−1; FIANEG).

Similarly prepared were tert-Butyl 4-(6,7-difluoro-1H-indol-3-yl)-(2S,4R)-2-methyl-1-piperidinecarboxylate and tert-butyl 4-(6, 7-difluoro-1H-indol-3-yl)-(2R,4S)-2-methyl-1-piperidinecarboxylate $^1$H NMR (CDCl$_3$), (ppm);1.16–1.34 (m, 3H), 1.52 (s, 9H), 1.60–1.92 (m, 2H), 1.94–2.36 (m, 2H), 2.96–3.38 (m, 2H), 3.80–4.32, (m, 1H), 4.36–4.74 (m, 1H), 6.82–7.00 (m, 2H), 7.18–7.30 (m, 1H); MS, reqd. 250.1; obs. 251.1 (M+1; FIAPOS); 249.1 (M−1; FIANEG).

tert-Butyl 4-(6-fluoro-7-methyl-1H-indol-3-yl)-(2S, 4R)-2-methyl-1-piperidinecarboxylate and tert-butyl 4-(6-fluoro-7-methyl-1H-indol-3-yl)-(2R,4S)-2-methyl-1-piperidinecarboxylate $^1$H NMR (CDCl$_3$), δ (ppm); 1.24–1.32 (m, 3H), 1.48 (s, 9H), 1.56–1.70 (m, 1H), 1.78–1.96 (m, 2H), 1.98–2.10 (m, 1H), 2.38 (s, 3H), 2.96–3.24 (m, 2H), 4.08 (br. s, 1H), 4.52 (br. s, 1H), 6.82–6.96 (m, 2H), 7.34–7.40 (m, 1H), 7.82 (br. s, 1H).

6-Fluoro-3-[(2S,4R)-2-methylpiperidin-4-yl]-1H-indole and 6-fluoro-3-[(2R,4S)-2-methylpiperidin-4-yl]-1H-indole tert-Butyl (2S,4R)-4-(6-fluoro-1H-indol-3-yl)-2-methyl-1-piperidinecarboxylate (1.21 g, 3.64 mmol) is dissolved in trifluoroacetic acid (50 ml) and dichloromethane (50 ml) and the mixture stirred at room temperature under nitrogen for 1 hour. The reaction is then quenched by the cautious addition of saturated aqueous sodium bicarbonate (500 ml), and the mixture extracted with ethyl acetate (2×250 ml). The organic layers are combined, dried over $MgSO_4$, then the solvent is removed in vacuo. This affords the desired product as a clear oil (0.84 g, 100% yield). $^1$H NMR ($CD_3OD$), δ (ppm); 1.06 (d, 3H), 1.60–1.70 (m, 1H), 1.72–1.98 (m, 3H), 2.72–2.90 (m, 2H), 2.92–3.12 (m, 1H), 3.14–3.24 (m, 2H), 6.6 (t, 1H), 6.9 (d, 1H), 6.94 (d, 1H), 7.34 (d.d, 1H); MS, reqd. 232.1; obs. 233.1 (M+1; FIAPOS); 231.1 (M−1; FIANEG).

Similarly prepared were

6-Fluoro-7-methyl-3-[(2S,4R)-2-methylpiperidin-4-yl]-1H-indole and 6-fluoro-7-methyl-3-[(2R,4S)-2-methylpiperidin-4-yl]-1H-indole $^1$H NMR (($CD_3)_2SO$), δ (ppm); 1.02–1.10 (m, 3H), 1.50–1.92 (m, 4H), 2.34 (s, 3H), 2.66–2.88 (m, 2H), 2.94–3.08 (m, 1H), 3.18–3.28 (m, 1H), 6.70–6.84 (m, 1H), 7.08 (s, 1H), 7.24–7.36 (m, 1H).

6,7-Difluoro-3-[(2S,4R)-2-methylpiperidin-4-yl]-1H-indole and 6,7-difluoro-3-[(2R,4S)-2-methylpiperidin-4-yl]-1H-indole (as a mixture)

The synthesis of the above compound was carried out in the same manner as that use to synthesise the 6-fluoro analogue. No HPLC was carried out, and instead, column chromatography (silica gel, eluted with 98% dichloromethane, 2% methanol and 0.2% aqueous ammonia) afforded the trans isomers as a racemic mixture. $^1$H NMR ($CDCl_3$), δ (ppm); 1.18 (d, 3H), 1.60–1.92 (m, 2H), 1.96–2.12 (d, 2H), 2.34 (br.s, 2H), 2.78–3.12 (m, 2H), 3.14–3.28 (m, 1H), 3.32–3.46 (m, 1H), 6.80–7.06 (m, 2H), 7.18–7.30 (m, 1H); MS, reqd. 250.1; obs. 251.1 (M+1; FIAPOS); 249.1 (M−1; FIANEG).

(1-Methylethyl)sulfamic Acid

A 250 ml 3-necked round bottom flask equipped with a magnetic stirrer bar, pressure equalising dropping funnel, thermometer and nitrogen gas bleed was charged with nitromethane (75 ml) and fuming sulfuric acid (30 g, i.e. oleum 12–17%). The mixture was cooled to 0° C. using an external cardice (solid $CO_2$)/acetone bath. Then isopropyl isocyanate (25 g, 0.294 mol) was added dropwise to the mixture, stirred under nitrogen, keeping the temperature below 30° C. during the addition. The stirred suspension was then heated under reflux for 30 mins, then allowed to cool to room temperature and stirred overnight. Diethyl ether (100 ml) was added to the mixture, which was then filtered. The filter pad was washed with more ether (3×100 ml) and then dried in an air stream at room temperature to give a pale yellow crystalline solid, (1-methyl ethyl)sulfamic acid. (JOC 1976 41 (25) 4028–9)

(1-Methylethyl)sulfamoyl chloride

A 500 ml 3-necked round bottom flask equipped with a water condenser, thermometer and magnetic stirrer bar was charged with (1-methyl ethyl)sulfamic acid (34.8 g, 0.25 mol), phosphorus pentachloride (52.06 g, 0.25 mol) and toluene (400 ml). The mixture was warmed under reflux for 1 hr, then cooled back down to room temperature. The solvent was removed in vacuo to give a pale brown oil which was then purified by distillation under reduced pressure (approximately 15 mm Hg and 110° C.) to give a clear, colourless liquid, (1-methyl ethyl)sulfamoyl chloride (JOC 1976 41 (25) 4028–9)

N-(4-Methylthiophenyl)-2,2-dimethylmalonamic acid

Thionyl chloride (8.15 g, 5 ml, 0.069 mol) was added to a stirred solution of 2,2-dimethylmalonic acid (7.26 g, 0.055 mol) in dry THF (55 ml). The mixture was heated under reflux for 3 hr. The reaction mixture was cooled to room temperature and 4-methylthioaniline (15.3 g, 0.11 mol) in THF (30 ml) was then added dropwise over 30 mins to the solution. The mixture was stirred at room temperature for 2 hr. The reaction mixture was then concentrated in vacuo and then treated with hydrochloric acid (2N, 100 ml). The product was extracted with ethyl acetate (2×100 ml). The organic extracts were combined, then washed with water (100 ml) and saturated sodium hydrogen carbonate solution (5×80 ml). The organic layer was then acidified with hydrochloric acid (5N, 250 ml) and the resultant white crystalline precipitate was collected by filtration to afford N-(4-methylthiophenyl)-2,2-dimethylmalonamic acid. mp 130–132° C.

N-(4-Methylthiophenyl)-N'-(1-methylethyl)sulfamide (1-Methylethyl)sulfamoyl chloride (6.63 g, 0.034 mol) was added dropwise to a solution of 4-(methylthio) aniline (4.48 g, 0.032 mol) and triethylamine (4.87 ml, 0.035 mol) in dry dichloromethane (100 ml) at 0° C. under a nitrogen atmosphere. After addition, the resultant mixture was allowed to warm to room temperature and was stirred for 6 hr. The reaction mixture was further extracted with dichloromethane and the organic extracts washed with water (2×50 ml), dried ($MgSO_4$) and concentrated in vacuo to yield N-(4-methylthiophenyl)-N'-(1-methylethyl)sulfamide as a white solid. δ (1H NMR, DMSO, ppm): 0.8 (6H, d), 2.3 (3H, s), 3.2 (1H, m), 3.35 (1H, s), 6.9–7.1 (4H, m), 9.5 (1H, s). M.P. 65–68° C.

3,4-Dihydro-3-(1-methylethyl)-6-methylthio-1H-2,1,3-benzothiadiazine-2,2-dioxide N-(4-Methylthiophenyl)-N'-(1-methylethyl)sulfamide (4.35 g, 0.016 mol) was dissolved in dry dichloromethane (150 ml) and methanesulphonic acid (18.87 ml, 0.303 mol). The solution was cooled at 0° C. before the addition of trioxan (0.480 g, 0.005 mol) in dichloromethane (15 ml). After stirring at 0° C. for 1 hr, the reaction mixture was poured onto ice-water (250 ml), the layers separated, dried ($MgSO_4$) and concentrated in vacuo to yield 3,4-dihydro-6-(ethylsulfonyl)-3-(1-methylethyl)-1H-2,1,3-benzothiadiazine-2,2-dioxide as a white solid. δ ($^1$H NMR, DMSO, ppm): 0.9 (6H, d), 2.3 (3H, s), 3.9 (1H, m), 4.5 (2H, s), 6.6 (1H, d), 7.0 (2H, m), 10.1 (1H, s)

3,4-Dihydro-3-(1-methylethyl)-6-(methylsulfonyl)-1H-2,1,3-benzothiadiazine-2,2-dioxide A solution of OXONE® (potassium peroxymonosulfate) (5.65 g, 0.0092 mol) in water was added to a solution of 3,4-dihydro-3-(1-methylethyl)-6-(methylthio)-1H-2,1,3-benzothiadiazine-2,2-dioxide (1 g, 0.0037 mol) in acetone/water (25 ml/2.5 ml) stirring at room temperature. After 30 mins, water (25 ml) and ethyl acetate (50 ml) were added to the mixture. The two layers were separated and the organic layer was then dried ($MgSO_4$) and concentrated in vacuo to afford 3,4-dihydro-3-(1-methylethyl)-6-(methylsulfonyl)-1H-2,1,3-benzothiadiazine-2,2-dioxide as a pale yellow solid. δ ($^1$H NMR, $CDCl_3$, 300 MHz, ppm): 1.0 (3H, d), 2.9 (3H, s), 4.1 (1H, m), 4.6 (2H, s), 6.8 (1H, d), 7.6 (2H, m), 9.9 (1H, s).

3,3-Dimethyl-6-methylthio-2,4-(1H,3H)-quinolinedione

Phosphorus pentoxide (4.49 g, 0.032 mol) was added to a stirred solution of N-(4-methylthiophenyl)-2,2-dimethylmalonamic acid (5.0 g, 0.020 mol) in methane-sulfonic acid (35 ml). The reaction mixture was warmed to 70° C. and stirred for 90 mins. The product mixture was then cooled to room temperature and poured over ice. The product was extracted with ethyl acetate (2×200 ml). The organic extracts were combined, washed with water (200 ml), saturated sodium hydrogen carbonate solution (200 ml), dried (MgSO$_4$) and concentrated in vacuo to give 3,3-dimethyl-6-methylthio-2,4(1H,3H)-quinolinedione as a yellow solid. Mp 152° C.

3,4-Dihydro-3,3-dimethyl-6-methylthio-2(1H)-quinolinone

Triethylsilane (34.75 ml, 49.1 g, 0.042 mol) was added dropwise to a stirred solution of 3,3-dimethyl-6-methylthio-2,4(1H,3H)-quinolinedione (12.79 g, 0.054 mol) in trifluoroacetic acid (520 ml) under nitrogen at 60° C. The reaction was then allowed to cool slowly to room temperature and was stirred for 16 hr. The solvent was then evaporated in vacuo to afford a yellow residue. The residue was then poured into saturated potassium carbonate solution (200 ml). The product was extracted with ethyl acetate (3×150 ml). The organic extracts were combined, washed with water (200 ml), dried and concentrated in vacuo to afford 3,4-dihydro-3,3-dimethyl-6-methylthio-2(1H)-quinolinone as a yellow solid. Mp 154° C.

3,4-Dihydro-3-(1-methylethyl)-6-methylthio-1-(prop-2-en-1-yl)-1H-2,1,3-benzothiadiazine-2,2-dioxide 3,4-Dihydro-3-(1-methylethyl)-6-methylthio-1H-2,1,3-benzothiadiazine-2,2-dioxide (10 g, 0.0367 mol) was added to a suspension of sodium hydride (1.61 g, 60% dispersion) in dry dimethylformamide (200 ml) at room temperature under a nitrogen atmosphere. The pale grey suspension was stirred for ten mins, and then allyl bromide (3.49 ml, 0.0404 mol) was added in one portion. The reaction mixture was stirred at 80° C. for 3 hr. The mixture was then concentrated in vacuo to yield a brown residue. The residue was dissolved in ethyl acetate (50 ml) and washed with water (2×50 ml). The organic layer was then dried (MgSO$_4$) and concentrated in vacuo to afford 3,4-dihydro-3-(1-methylethyl)-6-methylthio-1-(prop-2-en-1-yl)-1H-2,1,3-benzothiadiazine-2,2-dioxide. δ ($^1$H NMR, DMSO, ppm): 1.1 (6H, d), 2.5 (3H, s), 4.1 (1H, m), 4.5 (2H, d), 4.7 (2H, s), 5.3 (1H, dd), 5.4 (1H, dd), 6.0 (1H, m), 7.0 (1H, d), 7.3 (2H, m).

Similarly prepared was 3,3-Dimethyl-5-methanesulphonyl-1-(prop-2-en-1-yl)-1,3 dihydro-2H-indol-2-one from 3,3-dimethyl-5-methanesulphonyl-1,3 dihydro-2H-indol-2-one [Lit. Ref. EP 0780388]:

δ ($^1$H NMR, CDCl$_3$, ppm); 1.45 (6H, s), 3.05 (3H, s), 4.35 (2H, d), 5.15–5.3 (2H, m), 5.75–5.9 (1H, m), 6.9 (1H, d), 7.75 (1H, s), 7.85 (1H, m)

[3,4-Dihydro-2,2-dioxido-3-(1-methylethyl)-6-methylsulfonyl-1H-2,1,3-benzothiadiazin-1-yl] ethanal 3,4-Dihydro-3-(1-methylethyl)-6-methylthio-1-(prop-2-en-1-yl)-1H-2,1,3-benzothiadiazine-2,2-dioxide (10 g, 0.032 mol) was dissolved in dioxan (100 ml) and water (20 ml). Osmium tetroxide (2 crystals) was added to the solution and the mixture was stirred for five mins at room temperature, before the addition of sodium periodate (34.28 g, 0.160 mol) dissolved in water (25 ml). After stirring at ambient temperature for 14 hr, the reaction mixture was filtered through celite. The filtrate was then concentrated in vacuo to yield an oil. The oil was dissolved in ethyl acetate (100 ml) and washed with water (2×50 ml). The organic layer was then dried and concentrated in vacuo to afford [3,4-dihydro-2,2-dioxide-3-(1-methylethyl)-6-methylsulfonyl-1H-2,1,3-benzothiadiazin-1-yl]ethanal as a yellow solid. δ ($^1$H NMR, DMSO, ppm): 1.1 (6H, d), 3.2 (3H, s), 4.0 (1H, m), 4.8 (2H, s), 4.9 (2H, s), 7.0 (1H, d), 7.7 (1H, dd), 7.8 (1H, d), 9.6 (1H, s).

Similarly prepared was 3,3-Dimethyl-5-methanesulphonyl-1,3 dihydro-2H-indol-1-yl-2-one Ethanal from 3,4-dihydro-3-(1-methylethyl)-6-methylthio-1-(prop-2-en-1-yl)-1H-2,1,3-benzothiadiazine-2,2-dioxide δ ($^1$H NMR, CDCl$_3$, ppm); 1.45 (6H, s), 3.05 (3H, s), 4.9 (2H, s), 6.9 (1H, d), 7.7 (1H, s), 7.9 (1H, m), 9.6 (1H, s).

1-(2-Chloroethyl)-3,4-dihydro-3-(1-methylethyl)-6-methylthio-1H-2,1,3-benzothiadiazine-2,2-dioxide To a 250 ml 3 necked flask equipped thermometer, pressure equalised dropping funnel, nitrogen bubbler and magnetic stirrer bar was added 60% sodium hydride (1.77 g, 1.062 g, 0.04425 mol,) hexane washed, to dry DMF (75 ml). To this stirred suspension was added dropwise a solution of 3,4-dihydro-3-(1-methylethyl)-6-methylthio-1H-2,1,3-benzothiadiazine-2,2-dioxide (10.0 g, 0.0368 mol) in dry DMF (75 ml) (slight exotherm). The suspension was stirred under nitrogen for 2 hr until hydrogen evolution ceased. 1-Bromo-2-chloroethane (6.33 g, 3.77 ml, 0.04425 mol) was added dropwise and the reaction mixture allowed to stir at room temperature under nitrogen overnight. The reaction mixture was poured onto ice-water (800 ml) with stirring for 1 hr, filtered and washed with water (200 ml) to leave a white solid which was dried in vacuo at 50° C. to give a solid. Mp 74–75° C.

5-Methylthio-2-nitrobenzoic acid

5-Chloro-2-nitrobenzoic acid (25.2 g, 0.125 mol) was stirred in water. To this was added sufficient sodium hydroxide solution (2M, 42 ml, 0.084 mol) to dissolve the acid completely. A solution of sodium sulfide nonahydrate (33.0 g, 0.1375 mol) in water (75 ml) was added and the solution was stirred at 60° C. for 2.5 hr. This resultant red solution was added to a solution of sodium hydroxide (50% 10 ml, 0.125 mol) in water (15 ml), dimethyl sulfate (24 ml, 0.25 mol) was added and the solution heated under reflux for 1 hour. The solution was cooled and acidified with hydrochloric acid (5M, 32 ml, 0.16 mol). The precipitated yellow solid was filtered off, washed with water, dried at 60° C. under vacuum, mp 173° C. (lit. J. Heterocyclic Chemistry 1981 18 117). Mp 175–178° C.)

Methyl 4-methylthio-2-nitro benzoate

To a suspension of 4-methylthio-2-nitro benzoic acid (10 g; 0.047 mol) [Lit. Ref. DE 2421541] in dry dimethylformamide (300 mL) was added potassium carbonate (8.43 g; 0.061 mol) and iodomethane (6.41 mL; 0.103 mol) and the solution stirred at room temperature for 24 hrs. The reaction was poured into water and extracted with ether (3×500 mL). The combined organic extracts were washed with water, dried over anhydrous magnesium sulphate, filtered and the solvent removed under vaccuo to yield a yellow solid. This was dried at 50° C. under vacuum. (10.4 g; 97.5%)

$^1$H NMR (CDCl$_3$), δ (ppm); 2.5 (s, 3H), 3.85 (s, 3H), 7.25–7.3 (m, 2H), 7.85 (d, 1H)

Methyl 2-amino-4-methylthio benzoate

Methyl 4-methylthio-2-nitro benzoate (10.4 g; 0.046 mol) was dissolved in ethanol and Raney nickel added as an aqueous suspension. The solution was hydrogenated at 60 psi on a Parr hydrogenator for 6 hrs. The catalyst was filtered off through celite, washed with ethanol to give the product which was used directly in the next step. (8.9 g; 98%)

$^1$H NMR (CDCl$_3$), δ (ppm); 2.4 (s, 3H), 3.9 (s, 3H), 5.75 (br s, 2H), 6.6 (d, 1H), 7.3 (dd, 1H), 7.9 (d, 1H)

Methyl 2-methylsulphonylamino-4-methylthio benzoate

To a stirred solution of methyl 2-amino-4-methylthio benzoate (11.53 g; 0.0585 mol) in dry pyridine (60 mL) was added slowly over a 5 minute period methane sulphonyl chloride (4.98 mL; 0.0643 mol). An exotherm was produced taking the internal temperature to 35° C. After stirring overnight at room temperature, the pyridine was removed under vaccuo and water (150 mL) was added. Concentrated hydrodrochloric acid was added to pH2 and the product was extracted with ethyl acetate (3×100 mL). The organic extracts were washed with water (2×100 mL), 2N HCl (2×100 mL) and water (2×100 mL). After drying with anhydrous magnesium sulphate, filtering and removing the solvent, the product was isolated as a red oil which solidified on standing. (15.6 g; 97%)

$^1$H NMR (CDCl$_3$), δ (ppm); 2.5 (s, 3H), 3.05 (s, 3H), 3.95 (s, 3H), 7.47 (dd, 1H), 7.7 (d, 1H), 7.95 (d, 1H), 10.25 (s, 1H)

Methyl 2-(N-(prop-2-en-1-yl)-N-methylsulphonyl) amino-4-methylthio benzoate

To a solution of methyl 2-methylsulphonylamino-4-methylthio benzoate (6.9 g; 0.025 mol) in dry dimethylformamide (120 mL) was added anhydrous potassium carbonate (34.4 g; 0.25 mol) and tetrabutylammonium bromide (0.81 g; 2.51 mmol). Allyl bromide (20 equivalents) was added in one portion and the solution was stirred overnight at room temperature. The reaction was poured into water and the product extracted with ethyl acetate. The organic extracts were washed with water, dried over anhydrous magnesium sulphate, filtered and he solvent removed to give an oil. Column chromatography eluting with 20%–50% ethyl acetate-hexane gave a clear oil (7.2 g; 92%).

$^1$H NMR (CDCl$_3$), δ (ppm); 2.5 (s, 3H), 3.05 (s, 3H), 3.9 (s, 3H), 4.65 (d, 2H), 5.25–5.4 (m, 2H), 5.8–6.0 (m, 1H), 7.26 (d, 1H), 7.35 (m, 1H), 7.75 (d, 1H)

6-Methylthio-1-(prop-2-en-1-yl)-1H-2,1-benzothiazine-4-(3H)-one 2,2-dioxide

To a solution of sodium hydride (1.32 g; 0.0552 m of 50% dispersion in paraffin oil) in dry dimethylformamide (60 mL) was slowly added under nitrogen at 0° C. a solution of methyl 2-(N-(prop-2-en-1-yl)-N-methylsulphonyl)amino-4-methylthio benzoate (7.2 g;0.023 mol) in dry dimethylformamide (15 ml). After stirring overnight at room temperature the reaction was poured into ice water and the product extracted with ethyl acetate, washed repeatedly with water and dried over magnesium sulphate. After filtering and removal of the solvent, the oil was chromatographed on silica eluting with 20% ethyl acetate to give the product, 4.2 g; 65%)

$^1$H NMR (CDCl$_3$), δ (ppm); 2.53 (s, 3H), 4.3 (s, 2H), 4.55 (m, 2H), 5.3–5.47 (m, 2H), 5.85–6.0 (m, 1H), 7.25 (d, 1H), 7.5 (dd, 1H), 7.95 (d, 1H)

3,3-Dimethyl-6-methylthio-1-prop-2-en-1-yl -1H-2,1-benzothiazine-4-(3H)-one 2,2-dioxide 1-(Prop-2-en-1-yl)-6-methylthio-benzothiazine-4-one 2,2-dioxide (2.07 g; 0.0067 mol) was dissolved in dry dimethylformamide (50 mL) and potassium carbonate (2.03 g; 0.0147 mol) added followed by iodomethane (1.25 mL; 0.02 mol). The reaction was stirred overnight at room temperature and water was added. The product was extracted with ethyl acetate and, after washing with water and drying over magnesium sulphate the product was isolated as a solid (2.0 g; 89%)

$^1$H NMR (CDCl$_3$), δ (ppm); 1.65 (s, 6H), 2.5 (s, 3H), 4.55 (d, 2H), 5.3–5.5 (m, 2H), 5.9–6.1 (m, 1H), 7.05 (d, 1H), 7.45 (dd, 1H), 8.0 (d, 1H)

3,3-Dimethyl-6-methylthio-1-(prop-2-en-1-yl)-1H-2,1-benzothiazine 2,2-dioxide 1-(prop-2-en-1-yl)-3,3-dimethyl-6-methylthio-1H-2,1-benzothiazine-4-(3H)-one 2,2-dioxide (2 g; 0.006 mol) was dissolved in methanol (40 mL) and sodium borohydride (0.45 g; 0.012 mol) was added in one portion. After the initial effervescence, the reaction was left stirring overnight. The solvent was removed under vaccuo, water added and the product extracted with chloroform. After washing the organic extracts with water, drying over magnesium sulphate and filtering, the product was isolated as a white solid (1.8 g; 90%) of 3,4-dihydro-3,3-dimethyl-6-methylthio-1-(prop-2-en-1-yl)-1H-2,1-benzothiazin-4-ol 2,2-dioxide, used immediately in the next step.

$^1$H NMR (CDCl$_3$), δ (ppm); 1.4 (s, 3H), 1.6 (s, 3H), 2.5 (s, 3H), 3.35 (dd, 1H), 4.25–4.55 (m, 2H), 4.6–4.7 (dd, 1H), 5.3–5.5 (m, 1H), 6.9 (d, 1H), 7.22 (dd, 1H), 7.4 (d, 1H)

3,4-Dihydro-1-(prop-2-en-1-yl)-3,3-dimethyl-6-methylthio-1H-2,1-benzothiazin-4-ol 2,2-dioxide (1.8 g; 0.0053 m) was dissolved in trifluoroacetic acid (30 mL) and triethylsilane (15 mL) was added in one portion. After stirring for 4 hrs, the reaction was reduced to an oil under vaccuo and after the addition of saturated sodium bicarbonate, the product extracted with dichloromethane, dried, filtered and isolated as a colourless solid.(1.6 g; 93%)

$^1$H NMR (CDCl$_3$), δ (ppm); 1.45 (s, 6H), 2.4 (s, 3H), 4.4 (d, 2H), 5.25–5.5 (m, 2H), 5.9–6.03 (m, 1H), 6.85 (d, 1H), 7.05 (d, 1H), 7.15 (dd, 1H)

3,4-Dihydro-3,3-dimethyl-1-(prop-2-en-1-yl)-6-sulphonylmethyl-1H-2,1-benzothiazine 2,2-dioxide 3,4-Dihydro-3,3-dimethyl-6-methylthio-1-(prop-2-en-1-yl)-1H-2,1-benzothiazine 2,2-dioxide (1.6 g;0.00539 mol) was dissolved in acetone (50 mL) and oxone (7.29 g; 0.01185 mol) in water (20 mL) was added. The solution went opaque and was stirred for 30 min at room temperature. The acetone was removed on the rotary and water and ethyl acetate were added. The product was extracted with ethyl acetate (2×100 mL) and the organic extracts washed with water (2×100 mL). After drying, filtering and removal of solvent, a solid was isolated (1.2 g; 68%)

$^1$H NMR (CDCl$_3$), δ (ppm); 1.5 (s, 6H), 3.05 (s, 3H), 3.35 (d, 2H), 4.57 (m, 2H), 5.35–5.55 (m, 2H), 5.87–6.0 (m, 1H), 7.05 (d, 1H), 7.68 (dd, 1H), 7.75 (dd, 1H)

[3,4-Dihydro-3,3-dimethyl-6-sulphonylmethyl-1H-2,1-benzothiazin-1-yl 2,2-dioxide]ethanal To 3,4-dihydro-3,3-dimethyl-1-(prop-2-en-1-yl)-6-sulphonylmethyl-1H-2,1-benzothiazine 2,2-dioxide (1.2 g; 0.00365 mol) dissolved in tetrahydrofuran (100 ml) was added sodium periodate (1.56 g; 0.0073 mol) dissolved in water (20 ml) with warming. A crystal of osmium tetroxide was added and the solution stirred at room temperature overnight. Water was added and the product was extracted with ethyl acetate (3×100 ml). The organic extracts were collected, washed with water, dried over anhydrous magnesium sulphate, filtered and the solvent removed in vaccuo to give a gum. (1.0 g; 83%)

¹H NMR (CDCl₃), δ (ppm); 1.53 (s, 6H), 3.05 (s, 3H), 3.38 (d, 2H), 4.73 (s, 2H), 6.7 (dd, 1H), 7.7–7.8 (m, 2H), 9.75 (s, 1H)

1-(2-Chloroethyl)-3,4-dihydro-3-(1-methylethyl)-6-methysulfonyl-1H-2,1,3-benzothiadiazine-2,2-dioxide A 500 mL 3 necked flask equipped thermometer, pressure equalised dropping funnel, nitrogen bubbler and magnetic stirrer bar was charged with 1-(2-chloroethyl)-3,4-dihydro-3-(1-methylethyl)-6-methylthio-1H-2,1,3-benzothiadiazine-2,2-dioxide (10.0 g, 0.0299 mol) and chloroform (200 ml). To this solution was added in one portion m-chloroperbenzoic acid (20.6 g, ~4 equivalents, nominal purity 56–86%), this resulted in an exotherm which raised the temperature from 20° C. to 50° C. This solution was then stirred for 15 mins, water (100 ml) was added then 2M sodium hydroxide (100 ml). The organic layer was separated, washed again with 2M sodium hydroxide (100 ml), then water (100 ml) dried (MgSO₄), filtered and the filtrate evaporated under reduced pressure to leave a white-cream foam, which was dried at 45° C. in vacuo to yield the product.

δ (¹H NMR, CDCl₃, ppm): 7.8 (1H, d), 7.7 (1H, s), 7.1 (1H, d), 4.7 (2H, s), 4.2 (1H, m), 4.2 (2H, t), 3.0 (3H, s), 1.1 (6H, d).

1-(2-Chloroethyl)-3,4-dihydro-3,3-dimethyl-6-methylsulfonyl-2(1H)-quinolinone (Prepared from 1-(2-chloroethyl)-3,4-dihydro-3,3-dimethyl-6-methylthio-2(1H)-quinolinone.

δ (¹H NMR, CDCl₃, ppm): 7.8 (1H, dd), 7.7 (1H, d), 7.1 (1H, d), 4.2 (2H, t), 3.6 (2H, t), 3.0 (3H, s), 2.8 (2H, s), 1.1 (6H, s).

3,3-Dimethyl-1-{2-[(2R,4S)-4-(6-fluoro-1H-indol-3-yl)-2-methylpiperidinyl]ethyl}-6-(methylsulfonyl)-3,4-dihydro-1H-2,1-benzothiazine 2,2-dioxide To a stirred solution of 6-fluoro-3-[(2R,4S)-2-methylpiperidin-4-yl]-1H-indole (0.71 g; 0.0033 mol) and [3,3-dimethyl-6-sulphonylmethyl-1H-2,1-benzothiazin-1-yl 2,2-dioxide]ethanal in dry tetrachloroethane (70 ml) was added glacial acetic acid (6 drops). The solution was stirred for 10 mins at room temperature and sodium triacetoxyborohydride (0.76 g; 0.0036 mol) was added in one portion and the solution stirred rapidly at room temperature overnight. The reaction was poured into water and the product extracted with dichloromethane. The organic extracts were washed with water(2×100 ml) and dried over anhydrous magnesium sulphate. After filtration, the solvent was removed in vaccuo to give a yellow oil. Flash chromatography on silica eluting with 75%–90% ethyl acetate-hexane mixtures gave product as a yellow solid. (1.0 g; 62.5%)

¹H NMR (CDCl₃), δ (ppm); 1.5 (s, 6H), 2.6 (m, 2H), 2.85 (m, 4H), 3.05 (s, 3H), 3.3 (m, 4H), 4.1 (m, 2H), 6.15 (s, 1H), 6.9 (dt, 1H), 7.05 (dd, 1H), 7.15 (d, 1H) 7.25 (d, 1H), 7.7 (d, 1H), 7.8 (m, 2H), 8.2 (s, 1H)

Similarly prepared were 3,3-Dimethyl-1-{2-[(2S,4R)-4-(6-fluoro-1H-indol-3-yl)-2-methylpiperidinyl]ethyl}-6-(methylsulfonyl)-3,4-dihydro-1H-2,1-benzothiazine 2,2-dioxide from 6-fluoro-3-[(2S,4R)-2-methylpiperidin-4-yl]-1H-indole 3,3-Dimethyl-1-{2-[(2S,4R)-4-(6-fluoro-7-methyl-1H-indol-3-yl)-2-methylpiperidinyl]ethyl}-5-methylsulphonyl-1,3-dihydro-2H-indol-2-one from 6-fluoro-3-[(2S,4R)-2-methylpiperidin-4-yl]-1H-indole ¹H NMR ((CD₃)₂SO), δ (ppm); 1.02–1.10 (m, 3H), 1.45 (6H, s), 1.50–1.92 (m, 4H), 2.34 (s, 3H), 2.66–2.88 (m, 2H), 2.94–3.08 (m, 1H), 3.05 (3H, s), 3.05–3.3 (m, 3H), 4.05–4.15 (m, 2H), 6.70–7.1 (m, 3H), 7.24–7.36 (m, 1H), 7.65 (1H, s), 7.8 (1H, m)

3,3-Dimethyl-1-{2-[(2R,4S)-4-(6-fluoro-7-methyl-1H-indol-3-yl)-2-methylpiperidinyl]ethyl}-5-methylsulphonyl-1,3-dihydro-2H-indol-2-one from 6-fluoro-3-[(2R,4S)-2-methylpiperidin-4-yl]-1H-indole 1-{2-[(2R,4S)-4-(6-Fluoro-1H-indol-3-yl)-2-methylpiperidinyl]ethyl}-3-isopropyl-6-(methylsulfonyl)-3,4-dihydro-1H-2,1,3-benzothiadiazine 2,2-dioxide and 1-{2-[(2S,4R)-4-(6-Fluoro-1H-indol-3-yl)-2-methylpiperidinyl]ethyl}-3-isopropyl-6-(methylsulfonyl)-3,4-dihydro-1H-2,1,3-benzothiadiazine 2,2-dioxide A racemic mixture of 6-fluoro-3-[(2S,4R)-2-methylpiperidin-4-yl]-1H-indole and 6-fluoro-3-[(2R,4S)-2-methylpiperidin-4-yl]-1H-indole (0.34 g, 1.46 mmol), 1-(2-chloroethyl)-3-isopropyl-6-(methylsulfonyl)-3,4-dihydro-1H-2,1,3-benzothiadiazine 2,2-dioxide (0.64 g, 1.74 mmol), sodium iodide (0.26 g, 1.75 mmol) and sodium carbonate (0.90 g, 8.49 mmol) are suspended in a mixture of water (50 ml) and acetonitrile (5 ml), and stirred at reflux under nitrogen for 72 hours. The mixture is then cooled to room temperature, water is added (100 ml), and the off white gum that has formed is extracted with ethyl acetate (2×100 ml). The combined organic layers are combined, dried over magnesium sulfate, and the solvent evaporated under reduced pressure. Column chromatography, using hexane (60%) and ethyl acetate (40%) as the eluent affords 0.45 g of the desired product (54.8% yield) as mixture of trans enantiomers. The enantiomers are subjected to chiral stationary phase HPLC (Chiralpak-AD column, eluted with 60% hexane, 40% isopropanol and 0.2% dmea, F/R: 1.0 ml/min) to resolve the two trans enantiomers (retention times=9.9 and 10.7 min). ¹H NMR (CDCl₃), δ (ppm); 1.02–1.22 (m, 9H), 1.68–2.12 (m, 4H), 2.70–2.92 (m, 4H), 3.0 (s, 3H), 3.06–3.26 (m, 2H), 3.94–4.04 (m, 2H), 4.14–4.24 (m, 1H), 5.68 (br. s, 2H), 6.82–6.92 (t, 1H), 6.94 (s, 1H), 7.00–7.08 (d, 1H), 7.50–7.60 (m, 1H), 7.72 (br. s, 1H), 7.80–7.90 (d, 2H), 8.12–8.26 (br. s, 1H). MS, reqd. 562.2; obs. 563.2 (M+1; FIAPOS); 561.2 (M−1; FIANEG).

1-{2-[(2R,4S)-4-(6,7-Difluoro-1H-indol-3-yl)-2-methylpiperidinyl]ethyl}-3-isopropyl-6-(methylsulfonyl)-3,4-dihydro-1H-2,1,3-benzothiadiazine 2,2-dioxide and 1-{2-[(2S,4R)-4-(6,7-difluoro-1H-indol-3-yl)-2-methylpiperidinyl] ethyl}-3-isopropyl-6-(methylsulfonyl)-3,4-dihydro-1H-2,1,3-benzothiadiazine 2,2-dioxide A racemic mixture of 6,7-difluoro-3-[(2S,4R)-2-methylpiperidinyl]-1H-indole and 6,7-difluoro-3-[(2R,4S)-2-methylpiperidin-4-yl]-1H-indole (0.73 g, 2.92 mmol), 1-(2-chloroethyl)-3-isopropyl-6-(methylsulfonyl)-3,4-dihydro-1H-2,1,3-benzothiadiazine 2,2-dioxide (1.28 g, 3.49 mmol), sodium iodide (0.52 g, 3.48 mmol) and sodium carbonate (1.80 g, 17.0 mmol) are suspended in a mixture of water (70 ml) and acetonitrile (7 ml), and stirred at reflux under nitrogen for 24 hours. The mixture is then cooled to room temperature, water is added (100 ml), and the off white gum that has formed is extracted with ethyl acetate (2×100 ml). The combined organic layers are combined, dried over magnesium sulfate, and the solvent evaporated under reduced pressure. Column chromatography, using hexane (50%) and ethyl acetate (50%) as the eluent affords 0.42 g of the desired product (20.8% yield) as mixture of trans enantiomers. The enantiomers are subjected to chiral stationary phase HPLC (Chiralpak AD eluted with 60% Ethanol, 40% Heptane and 0.2% dmea, F/R: 1.0 ml/min) to resolve the two trans enantiomers (retention times=14.7 and 16.4 min). $^1$H NMR (CDCl$_3$), δ (ppm); 1.02–1.18 (m, 3H), 1.36–1.52 (d, 6H), 1.86–2.00 (m, 1H), 2.00–2.10 (d, 1H), 2.12–2.20 (d, 1H), 2.34–2.44 (m, 1H), 2.50–2.62 (m, 1H), 2.70 (s, 1H), 3.06–3.14 (m, 3H), 3.18–3.30 (m, 2H), 3.32–3.50 (m, 1H), 3.90–3.98 (s, 1H), 4.10–4.12 (m, 1H), 4.54–4.78 (m, 4H), 6.92–7.00 (m, 1H), 7.12 (s, 1H), 7.30–7.36 (m, 1H), 7.70 (s, 1H), 7.92–7.98 (m, 1H), 8.56 (s, 1H); MS, reqd. 580.2; obs. 581.2 (M+1; FIAPOS).

Similarly prepared were

1-{2-[(2R,4S)-4-(6-Fluoro-1H-indol-3-yl)-2-methylpiperidinyl]ethyl}-3,3-dimethyl-6-(methylsulfonyl)-3,4-dihydro-2(1H)-quinolinone and 1-{2-[(2S,4R)-4-(6-Fluoro-1H-indol-3-yl)-2-methylpiperidinyl]ethyl}-3,3-dimethyl-6-(methylsulfonyl)-3,4-dihydro-2(1H)-quinolinone $^1$H NMR ((CD$_3$)$_2$SO), (ppm); 1.08–1.20 (m, 3H), 1.56–2.00 (m, 4H), 2.56 (s, 6H), 2.66–2.82 (m, 2H), 2.94 (s, 2H), 3.06–3.18 (m, 2H), 3.28 (s, 3H), 4.00–4.22 (m, 2H), 6.84–6.92 (t, 1H), 7.08–7.18 (m, 2H), 7.46–7.60 (m, 2H), 7.82–7.92 (m, 2H); MS, reqd. 511.3; obs. 512.3 (M+1; FIAPOS).

1-{2-[(2R,4S)-4-(6,7-Difluoro-1H-indol-3-yl)-2-methylpiperidinyl]ethyl}-3,3-dimethyl-6-(methylsulfonyl)-3,4-dihydro-2(1H)-quinolinone from 4-(6,7-difluoro-1H-indol-3-yl)-(2R,4S)-2-methylpiperidine.

$^1$H NMR (CDCl$_3$), δ (ppm); 1.05–1.20 (m, 3H), 1.6–2.00 (m, 4H), 2.55 (s, 6H), 2.58–2.80 (m, 2H), 2.94 (s, 2H), 3.06–3.18 (m, 2H), 3.3 (s, 3H), 4.00–4.20 (m, 2H), 6.80–7.06 (m, 2H), 7.1–7.3 (m, 2H), 7.6–7.8 (m, 2H)

1-{2-[(2S,4R)-4-(6,7-Difluoro-1H-indol-3-yl)-2-methylpiperidinyl]ethyl}-3,3-dimethyl-6-(methylsulfonyl)-3,4-dihydro-2(1H)-quinolinone from 4-(6,7-difluoro-1H-indol-3-yl)-(2S,4R)-2-methylpiperidine.

The following Examples illustrate formulations comprising an active ingredient according to the invention.

Example 2

Tablets each containing 10 mg of active ingredient are made up as follows:

| | |
|---|---|
| Active ingredient | 10 mg |
| Starch | 160 mg |
| Microcrystalline cellulose | 100 mg |
| Polyvinylpyrrolidone (as 10% solution in water) | 13 mg |
| Sodium carboxymethyl starch | 14 mg |
| Magnesium stearate | 3 mg |
| Total | 300 mg |

The active ingredient, starch and cellulose are mixed thoroughly. The solution of polyvinylpyrrolidone is mixed with the resultant powders and passed through a sieve. The granules so produced are dried and re-passed through a sieve. The sodium carboxymethyl starch and magnesium stearate are then added to the granules which, after mixing, are compressed on a tablet machine to yield tablets each weighing 300 mg.

Example 3

Capsules each containing 20 mg of active ingredient are made as follows:

| | |
|---|---|
| Active ingredient | 20 mg |
| Dried starch | 178 mg |
| Magnesium stearate | 2 mg |
| Total | 200 mg |

The active ingredient, starch and magnesium stearate are passed through a sieve and filled into hard gelatine capsules in 200 mg quantities.

Example 4

Capsules each containing 20 mg of medicament are made as follows:

| | |
|---|---|
| Active ingredient | 20 mg |
| Lactose | 171 mg |
| Sodium lauryl sulphate | 2 mg |
| Sodium starch glycollate | 6 mg |
| Magnesium stearate | 1 mg |
| | 200 mg |

The active ingredient, lactose, sodium lauryl sulphate and sodium starch glycollate are mixed thoroughly. The blend is mixed with the magnesium stearate and filled into hard gelatine capsules in 200 mg quantities.

Example 5

Tablets each containing 20 mg and medicaments are made as follows:

| | |
|---|---|
| Active ingredient | 20 mg |
| Lactose | 103 mg |
| Microcrystalline cellulose | 150 mg |
| Hydroxypropylmethylcellulose | 15 mg |
| Sodium starch glycollate | 9 mg |
| Magnesium stearate | 3 mg |
| | 300 mg |

The active ingredient, lactose, microcrystalline cellulose, sodium starch glycollate and hydroxypropylmethylcellulose are passed through a sieve and blended together. Water is added to the blended powders to form a damp mass. The damp mass is passed through a coarse screen, dried, then re-screened. The dried granules are mixed with the magnesium stearate and compressed into tablets of 300 mg weight.

What is claimed is:

1. A compound of the formula:

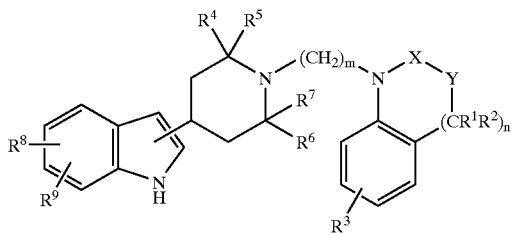

in which $R^1$ and $R^2$ are each hydrogen or $C_{1-6}$ alkyl, $R^3$ is —$SR^{10}$, —$SOR^{10}$, —$SO_2R^{10}$, —$COR^{10}$, —$CH_2OH$ or —$CONHR^{11}$, where $R^{10}$ is $C_{1-6}$ alkyl and $R^{11}$ is hydrogen or $C_{1-6}$ alkyl, $R^4$, $R^5$, $R^6$ and $R^7$ are each hydrogen or $C_{1-6}$ alkyl, provided that at least one of $R^4$, $R^5$, R6 and $R^7$ is $C_{1-6}$ alkyl, $R^8$ and $R^9$ are each hydrogen, halo, $C_{1-6}$ alkyl or cyano, n is 0 or 1 and m is 2 or 3, X is

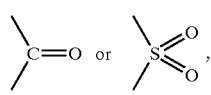

and

Y is

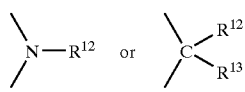

wherein $R^{12}$ and $R^{13}$ are each hydrogen, $C_{1-6}$ alkyl, cyclopropyl or cycopropyl-$C_{1-6}$ alkyl; and salts thereof.

2. A compound according to claim 1 of the formula:

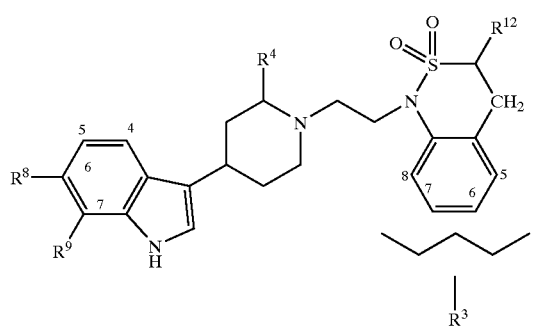

in which $R^8$ and $R^9$ are each hydrogen or fluoro, $R^3$ is at the 6- or 7- position and is —$SOR^{10}$, —$SO_2R^{10}$ or —$COR^{10}$, where $R^{10}$ is $C_{1-6}$ alkyl, $R^4$ is $C_{1-6}$ alkyl; and salts thereof.

3. A compound according to claim 1 of the formula

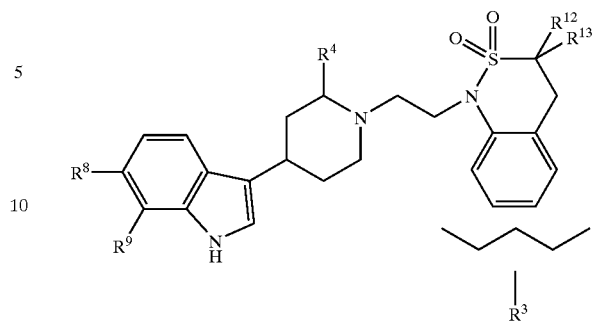

in which $R^8$ and $R^9$ are each hydrogen or fluoro, $R^3$ is in the 6- or 7-position and is —$SOR^{10}$, —$SO_2R^{10}$ or —$COR^{10}$, where $R^{10}$ is $C_{1-6}$ alkyl, $R^4$ is $C_{1-6}$ alkyl, and $R^{12}$ and $R^{13}$ are each hydrogen or $C_{1-6}$ alkyl; and salts thereof.

4. A compound according to claim 1 of the formula:

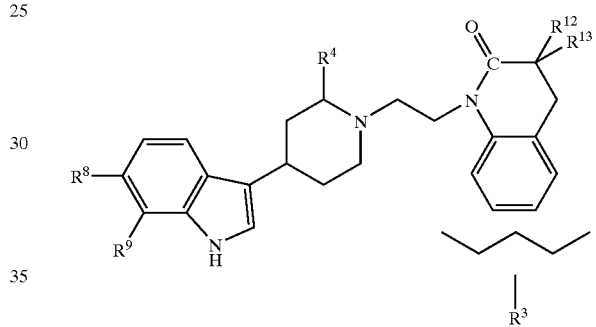

in which $R^8$ and $R^9$ are each hydrogen or fluoro, $R^3$ is in the 6- or 7-position end is —$SOR^{10}$, —$SO_2R^{10}$ or —$COR^{10}$, where $R^{10}$ is $C_{1-6}$ alkyl, $R^4$ is $C_{1-6}$ alkyl, and $R^{12}$ and $R^{13}$ are each hydrogen or $C_{1-6}$ alkyl; and salts thereof.

5. A compound according to claim 1 of the formula:

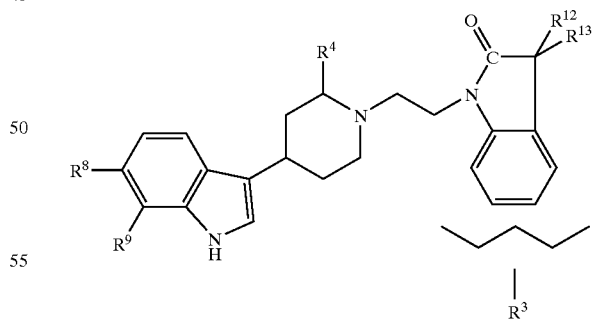

in which $R^8$ and $R^9$ are each hydrogen or fluoro, $R^3$ is in the 6- or 7-position and is —$SOR^{10}$, —$SO_2R^{10}$ or —$COR^{10}$, where $R^{10}$ is $C_{1-6}$ alkyl, $R^4$ is $C_{1-6}$ alkyl, and $R^{12}$ and $R^{13}$ are each hydrogen or $C_{1-6}$ alkyl; and salts thereof.

6. A pharmaceutical formulation comprising a compound according to claim 1, or a pharmaceutically acceptable salt thereof, together with a pharmaceutically acceptable diluent or carrier therefor.

7. A method of preparing a compound according to claim 1, which comprises reacting a compound of the formula

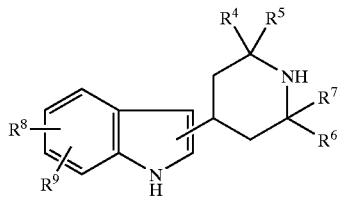

with a compound of the formula

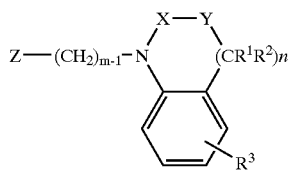

where (i) Z is —CH$_2$W, where W is a leaving group, or (ii) Z is —CHO.

8. A method of treating a human suffering from a disorder selected from the group consisting of depression, obesity, bulimia, alcoholism, pain, hypertension, sexual dysfunction, anxiety, schizophrenia, obsessive compulsive disorder, headache, emesis, and epilepsy, which comprises administering to said human an effective amount of a compound of formula I according to claim 1, or a pharmaceutically acceptable salt thereof.

* * * * *